US00PP26974P3

(12) United States Plant Patent
Bagdasarian

(10) Patent No.: US PP26,974 P3
(45) Date of Patent: Jul. 26, 2016

(54) STRAWBERRY PLANT NAMED 'LUCIA'

(50) Latin Name: *Fragaria×ananassa*
Varietal Denomination: Lucia

(71) Applicant: Jimmy Haig Bagdasarian, Santa Cruz, CA (US)

(72) Inventor: Jimmy Haig Bagdasarian, Santa Cruz, CA (US)

(73) Assignees: Jimmy H. Bagdassarian, Santa Cruz, CA (US); Lassen Canyon Nursery, Inc., Redding, CA (US)

( * ) Notice: Subject to any disclaimer, the term of this patent is extended or adjusted under 35 U.S.C. 154(b) by 175 days.

(21) Appl. No.: 13/998,533

(22) Filed: Nov. 6, 2013

(65) Prior Publication Data

US 2015/0128318 P1 May 7, 2015

(51) Int. Cl.
*A01H 5/08* (2006.01)

(52) U.S. Cl.
USPC ..... Plt./208

(58) Field of Classification Search
USPC ..... Plt./208, 209
CPC ..... A01H 5/0893
See application file for complete search history.

(56) References Cited

PUBLICATIONS

GTITM UPOVROM Citation for 'Lucia' as per QZ PBR 20061524; Oct. 15, 2006, 1 page.*

* cited by examiner

*Primary Examiner* — Kent L Bell
(74) *Attorney, Agent, or Firm* — Catherine Ashley Straight

(57) ABSTRACT

A new and distinct variety of strawberry plant named 'Lucia'. This new short day strawberry variety is characterized by very vigorous plants which produce long conical fruit of uniform shape and size, which has an exceptional, sweet strawberry flavor, and a very desirable lighter red exterior color. The variety is fully remontant in coastal areas of California.

7 Drawing Sheets

Latin name of the genus and species of the plant claimed: *Fragaria×ananassa.*

Variety denomination: 'Lucia'.

BACKGROUND OF THE INVENTION

1. Field of Invention

The present invention relates to a new and distinct variety of strawberry named 'Lucia'. This new short day strawberry variety is the result of a controlled cross in an ongoing breeding program made by the inventor, Jimmy Bagdasarian, in 2008. The variety is botanically known as *Fragaria×ananassa.*

The primary market for the 'Lucia' variety is for the fresh market sales of the fruit. 'Lucia' produces very high quality, large firm berries, which are attractive and which have excellent flavor. The berries produced by the 'Lucia' variety are sweet tasting, exhibiting excellent culinary qualities.

2. Description of Relevant Prior Art

The controlled cross, conducted in the ongoing breeding program, which resulted in the 'Lucia' variety was between a strawberry variety designated '5E10', a female, and a strawberry variety designated '16F29', a male. The female parent, '5E10', is an unreleased proprietary variety having the following plant characteristics: short day; compact growth habit; blistered, dark colored, high gloss leaves; with smaller size, short conical fruit having a dark red exterior and medium red interior color. The variety denomination of '16F29', the pollen parent, is 'Sweet Ann' (patented, U.S. Plant Pat. No. 22,472). The plant characteristics of 'Sweet Ann' are: day-neutral; globose with open plant density; strong vigor; leaves have medium glossiness with weak or absent blistering; with large size, conical fruit having a glossy medium red exterior and interior color.

The aforementioned controlled cross was carried out in a breeding program at Santa Cruz, Calif., USA. Pollen taken from a '16F29' plant pollinated a female '5E10' plant. The flowers were covered so that no other pollen could contaminate the procedure.

Strawberries developed, were later harvested and the seeds resulting from this cross were extracted and germinated in a greenhouse at Redding, Calif., USA. The resulting seedlings were transplanted to Shastina, Calif. in 2009, grown for an additional period of time and allowed to propagate asexually. Plants were then harvested and planted in breeding plots in early to mid-October in: Oxnard, Calif. (Ventura County); and Watsonville, Calif. (Monterey County). The selection of the new variety was first made in Watsonville, Calif., and designated '42J4' in 2010. This selection was later named 'Lucia'.

The new variety was further propagated asexually by stolons in breeding plots in: Macdoel, Calif. (Siskiyou County); and Manteca, Calif. (San Joaquin County).

The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, Calif.

The propagules of 'Lucia' ('42J4') are identical to the original plant in all distinguishing characteristics; accordingly, the propagation has demonstrated that the traits disclosed herein remain fixed and true to type through successive generations of asexual reproduction.

SUMMARY OF THE INVENTION

Lucia is a short day variety exhibiting the following combination of characteristics, which have been observed repeatedly, and which distinguish this strawberry plant as a new and distinct variety:

1. The variety produces large sized fruit;
2. The fruit is very well shaped, long conical;
3. The fruit is attractive, having a glossy medium red exterior and a light red interior;
4. The fruit is sweet tasting, with excellent flavor;
5. The variety produces a high volume of uniformly shaped conic fruit;
6. The plants of the variety are vigorous and maintain an open architecture; and,
7. The variety is fully remontant in a coastal environment.

The fruit produced by the 'Lucia' plant variety is larger than that of its female parent '5E10'. 'Lucia' produces fruit which is sweet, like its pollen parent 'Sweet Ann', however, 'Lucia' exhibits a more desirable ripening pattern as compared to 'Sweet Ann'. The fruit of 'Lucia' is also firmer than the fruit of either of its parent varieties: 'Sweet Ann' and '5E10'.

'Lucia' demonstrates other characteristics and qualities that are desired by fresh market strawberry sales companies. The lighter, medium red color is preferred by many shippers of fresh strawberries, as the darker berries are more likely to be viewed as overripe by buyers than the lighter colored berries. In addition, 'Lucia' plants have been grown in experimental plots with the fruit harvested and held in refrigeration; the fruit of 'Lucia' retained its firmness, color, gloss, and quality even after seven (7) days holding time.

The plant vigor of 'Lucia' is very high which provides an advantage over lower vigor varieties which require high fertility inputs to achieve similar vigor levels. 'Lucia' exhibits moderate to good disease and pest tolerance, even when grown in non-fumigated ground. 'Lucia' has also shown good results when grown under organic farming practices, which is the fastest growing segment in the California strawberry industry.

BRIEF DESCRIPTION OF THE DRAWING

The accompanying color photographs, identified as FIGS. 1 through 7, show the appearance of typical specimens of the new strawberry variety, initially designated '42J4', and now named 'Lucia'. These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Lucia' were taken in July of 2012.

DETAILED BOTANICAL DESCRIPTION OF THE PLANT

Figure 1:
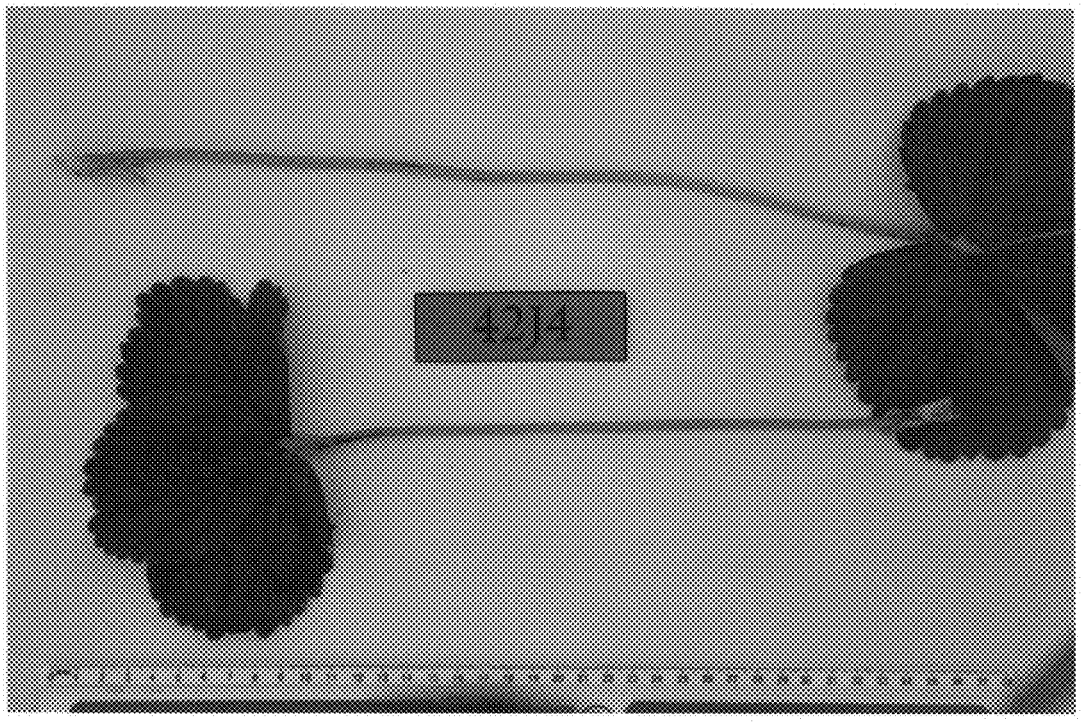
FIG. 1 shows typical leaf and petiole structures of 'Lucia' at mid-season.
Figure 2:
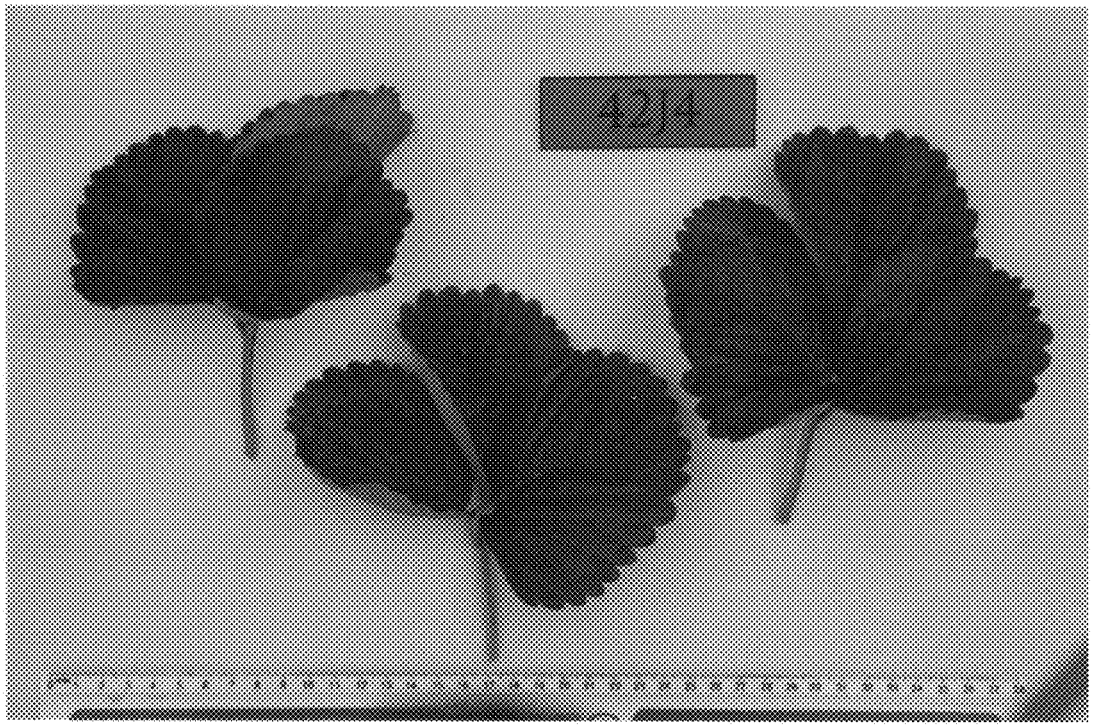
FIG. 2 shows typical leaf structure.
Figure 3:
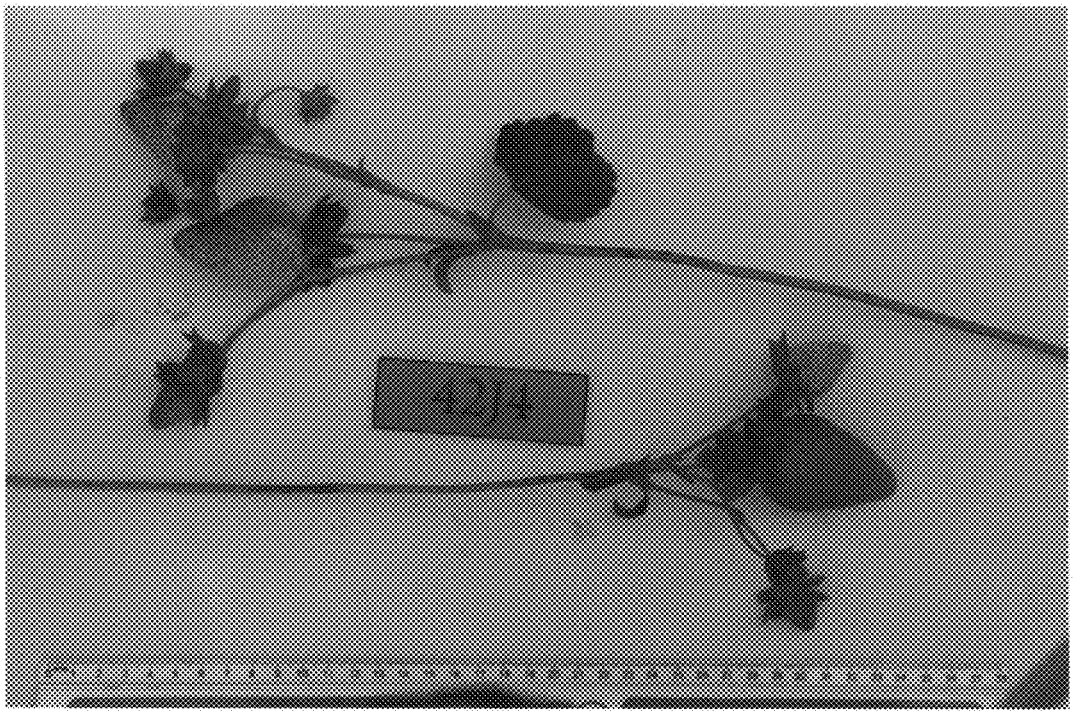
FIG. 3 shows a selection of typical mid-season fruit.
Figure 4:
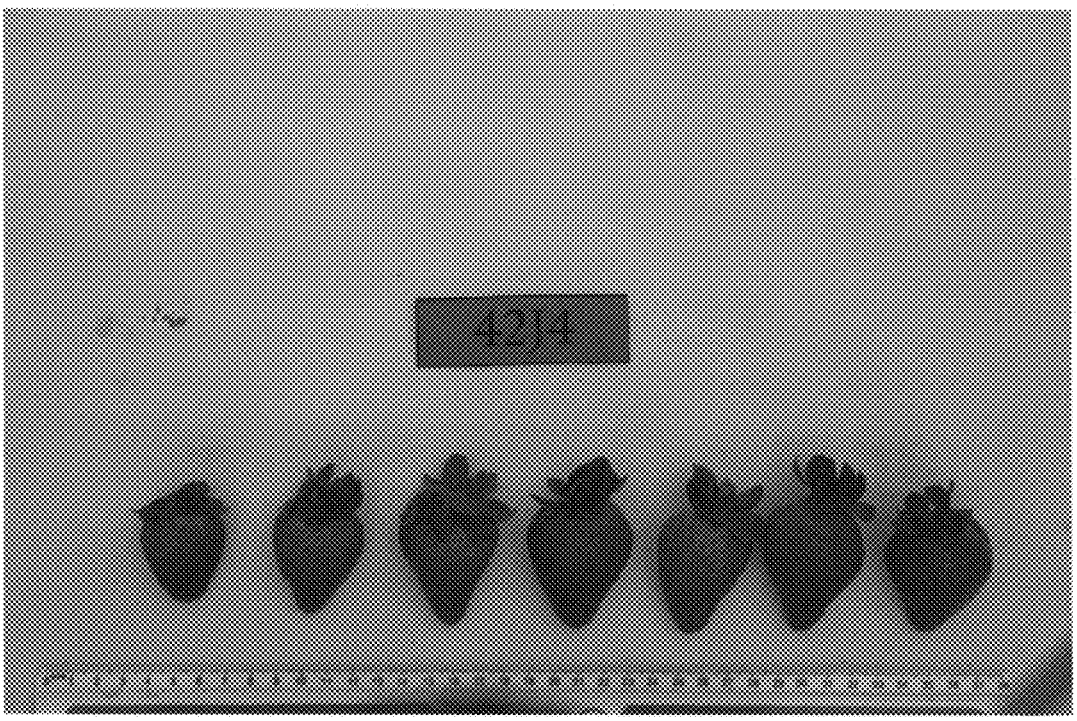
FIG. 4 shows typical fruit shape and calyx position over the berry of 'Lucia'.
Figure 5:
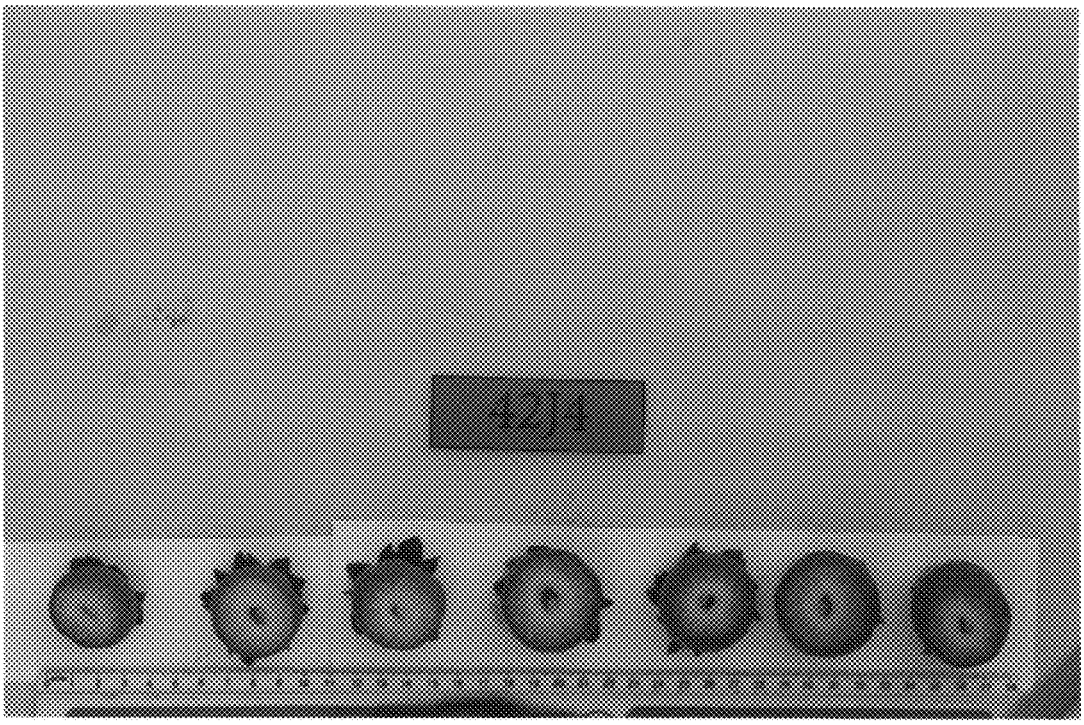
FIG. 5 shows a transverse cross-section of typical fruit internal coloration and core size.
Figure 6:
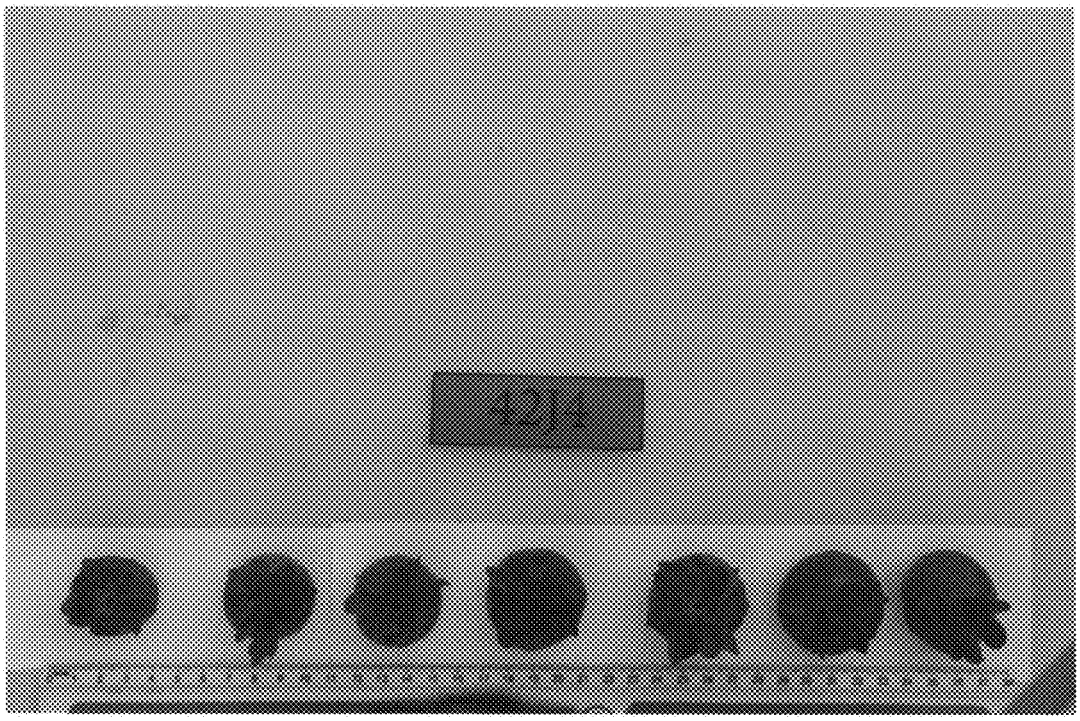
FIG. 6 shows calyx shape and relationship to fruit at mid-season.
Figure 7:
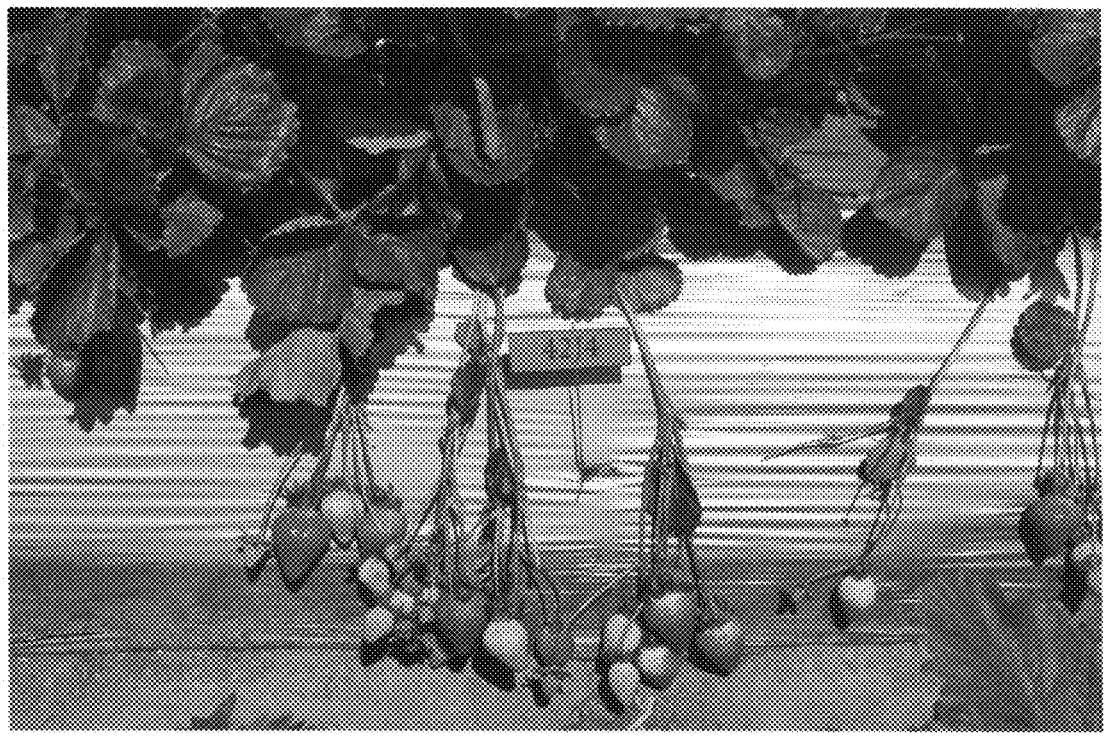
FIG. 7 shows typical fruiting plants in a field.

'Lucia' is a new and distinct variety of strawberry, genus and species *Fragaria×ananassa*. It is the result of a cross between its female parent, '5E10', an unreleased proprietary variety, and 'Sweet Ann', U.S. Plant Pat. No. 22,472, its male parent. '5E10' is a short-day variety with partially remontant tendencies and 'Sweet Ann' is a day-neutral variety. 'Lucia' is a short-day variety that has ever-bearing tendencies in temperate coastal environments, and is partially remontant in warmer inland environments. Stolons have been observed blooming in production fields, but bloom only once in a high elevation nursery, consistent with a short-day variety. The plants of the new variety are very vigorous and produce multiple crowns early after planting. 'Lucia' exhibits several characteristics which are improvements over one or both of its parent varieties, and other known cultivars. The characteristics of 'Lucia' were observed in plants aged seven to eight months from planting. These characteristics and comparisons with other cultivars are discussed following.

The fruiting pattern of 'Lucia' is similar to that of 'Sweet Ann', but production is slower in the early quarter of the season. The fruit size of 'Lucia' is uniformly medium large, slightly smaller than the large one hundred gram fruit produced by 'Sweet Ann', but larger than the fruit produced by '5E10'. This smaller size of fruit of 'Lucia' provides an advantage in Northern California production areas where early risk of rain damage is high.

The fruit produced by '5E10' is short conic with wide, broad shoulders, while both 'Lucia' and the male parent, 'Sweet Ann', produce long conic fruit. The fruit of 'Lucia' ripens more evenly from the tip to the shoulders of the berry, resulting in a more uniform red color over the whole fruit. In contrast, the shoulders of the fruit of 'Sweet Ann' are the last portion to ripen. The fruit of 'Lucia' is nearly absent of any creases and is smoother than the fruit of 'Sweet Ann'; and, it is also firmer than the fruit of either '5E10' or 'Sweet Ann'. The fruit of 'Lucia' holds in storage better than either of its parent varieties, and the fruit of 'Lucia' retains its gloss with less visible fruit bruising than observed with the fruit of 'Sweet Ann'.

The data set forth for 'Lucia' in Tables 1, 2, and 3 was collected in August 2012 from plants grown at the Meridian ranch test plot, in Prunedale, Monterey County, Calif. Color terminology where noted herein for 'Lucia' and 'Sweet Ann' is in accordance with the Pantone Color Formula Guide GP 1201.

In Table 1, the observed characteristics of 'Lucia' are set forth.

TABLE 1

| Detailed Description of Characteristics of 'Lucia' | |
|---|---|
| SPECIFICATION: | |
| Genus/Species | *Fragaria × Ananassa.* |
| Market name | Strawberry |

TABLE 1-continued

| Detailed Description of Characteristics of 'Lucia' | |
|---|---|
| PARENTS: | |
| Female | Proprietary variety '5E10'(unpatented). |
| Male | 'Sweet Ann' (U.S. Plant Pat. No. 22,472). |
| PLANT: | |
| Type | Short Day. |
| Growth habit | Semi-upright. |
| Foliage density | Dense. |
| Vigor | High. |
| Height | Average: 33.65 cm; range: 28 cm to 39 cm. |
| Width | Average: 47.25 cm; range: 43 cm to 55 cm. |
| Crowns | Multiple crowns produced early after planting. |
| Disease tolerance | Moderately tolerant to *Ramularia tulasnei* (common leaf spot) and *Sphaerotheca macularis* (powdery mildew). Exhibits good tolerance to *Tetranychus urticae* (two spotted spider mite), even when grown in non-fumigated ground. |
| LEAF: | |
| Width | Average: 19.55 cm; range: 16.5 cm to 21.5 cm. |
| Color | Adaxial Surface: green 364 U.<br>Abaxial Surface: green 363 U. |
| Pubescence | Medium density. |
| Inter-vein blistering | Medium. |
| Glossiness | High. |
| Variegation | None. |
| TERMINAL LEAFLET: | |
| Length | Average: 10.3 cm. |
| Width | Average: 9.13 cm. |
| Ratio length to width | 1.13. |
| Margin | Serrate to crenate. |
| Leaf shape | Orbicular. |
| Apex shape | Rounded. |
| Base shape | Rounded to obtuse. |
| Cross-section shape | Moderately concave. |
| PETIOLE: | |
| Pubescence | Medium density; direction: perpendicular. |
| Petiole color | Green 366 U. |
| Petiole length | Average: 26.85 cm. |
| Petiole diameter | Average: 4.48 mm. |
| STIPULE: | |
| Stipule anthocyanin coloration | Yes. |
| Stipule color | Green 376U. |
| Length | Average: 35.74 mm. |
| Width | Average: 17.8 mm. |
| STOLON: | |
| Number produced | Average: 15.9; range: 14 to 19. |
| Length | Average: 45.5 cm. |
| Stolon anthocyanin coloration | Present; medium intensity. |
| Stolon color | Red 1777 U. |
| Pubescence | Medium high; up-wards direction. |
| Diameter | Average: 4.0 mm; range: 3.5 mm to 4.4 mm. |
| INFLORESCENCE: | |
| Flowering time | Early. |
| Position | First bract at foliage level, bloom well above canopy. |
| Number of blooms | Average: 6.4; range:4 to 9. |
| Length | Average of fruiting clusters at mid-season: 43.05 cm. |
| Flower | Average diameter: 28.81 mm; range: 23.5 mm to 34.2 mm. |
| Petal arrangement | Touching to overlapping. |
| Petals | Average number per flower: 5 |
| Petal Shape | Orbicular. |
| Petal Apex | Rounded. |
| Petal Base | Obtuse. |
| Petal Margin | Entire. |

TABLE 1-continued

| Detailed Description of Characteristics of 'Lucia' | |
|---|---|
| Petal Length | Average: 12.44 mm; range: 10.6 mm to 14.2 mm. |
| Petal Width | Average: 11.86 mm; range: 10.0 mm to 13.1 mm. |
| Ratio length to width | 1.04. |
| Petal Color | Upper surface: bright white, 11-0601 TPX.<br>Under surface: bright white, 11-0601 TPX. |
| Calyx | Size in relation to corolla: slightly larger. |
| Calyx color | Adaxial Surface: green 364 U.<br>Abaxial Surface: green 371 U. |
| Sepal Number | Typical per flower: 11.<br>Observed per flower: 9 to 12. |
| Sepal Shape | Elliptical. |
| Sepal Apex | Convex. |
| Sepal Margin | Entire. |
| Sepal Length | Average: 17.5 mm. |
| Sepal Width | Average: 8.5 mm. |
| Stamens | Average number: 22.1; range 20 to 25. |
| Pedicel | Attitude of hairs is upwards/oblique. |
| FRUIT: | |
| Bearing | Remontant in coastal environments; partial remontance inland. |
| Shape | Consistently well-shaped, long conical. |
| Length | Average: 49.76 mm; range: 42.80 mm to 55.33 mm. |
| Width | Average: 38.05 mm; range: 32.10 mm to 41.50 mm. |
| Weight | Average grams per berry: 33.25 g. |
| Achenes | Approximately level with the fruit surface. |
| Glossiness | Strong. |
| External color | Red 1788 C |
| Internal color | Flesh, excluding core: red 179 C |
| Evenness of external color | All the way to the top of berry. |
| Width of band at top devoid of achenes | Small. |
| Fruit center | Some hollowness. |
| Yield | Average grams per plant: 1,057 g. |

The comparison statistics set forth in the following Tables are with respect to characteristics observed at mid-season. All measurements for 'Lucia' were taken at the Meridian ranch test plot in Prunedale, Monterey County, Calif. during mid-season 2012. In Tables 2 and 3, the characteristics of 'Lucia' are compared with the varieties 'Sweet Ann' (U.S. Plant Pat. No. 22,472) and 'Albion' (U.S. Plant Pat. No. 16,228). Color identifications where noted herein for 'Lucia' and 'Sweet Ann' are in accordance with the Pantone Color Formula Guide; the color identifications for 'Albion' are based on the Munsell system.

Plants and Foliage

The form and structure of the plants of 'Lucia' are similar to that of 'Sweet Ann' plants: erect and open. However, the plants of the 'Lucia' variety are slightly taller than those of 'Sweet Ann'. The plants of 'Lucia', like those of its parent 'Sweet Ann', have high vigor and are very large in comparison to many other commercial cultivars grown in fresh strawberry production fields in California. In Table 2, comparative data for foliar characteristics are presented for 'Lucia' and for two comparison cultivars, 'Sweet Ann' and 'Albion'.

TABLE 2

Foliar Characteristics of 'Lucia' Compared to 'Sweet Ann' and 'Albion'

| Foliar Characteristic | | 'Lucia' | Cultivar 'Sweet Ann' | 'Albion' |
|---|---|---|---|---|
| Plant height (mm) | Average | 391 | 380 | 252 |
| | Range | 292-490 | 290-480 | 210-270 |
| Plant spread (mm) | Average | 472 | 420 | 341 |
| | Range | 430-550 | 330-510 | 304-394 |
| Leaf width (mm) | Average | 195 | 165 | 135 |
| | Range | 165-220 | 130-195 | 105-170 |
| Mid-tier leaflet length (mm) | Average | 103 | 88 | 73 |
| | Range | 82-116 | 72-105 | 50-95 |
| Mid-tier leaflet width (mm) | Average | 91 | 67 | 68 |
| | Range | 73-102 | 52-88 | 50-95 |
| Petiole length (mm) | Average | 268 | 220 | 105 |
| | Range | 230-355 | 150-280 | 70-130 |
| Petiole diameter (mm) | Average | 4.48 | 3.74 | 4.1 |
| | Range | 3.70-5.80 | 3.01-4.29 | 3.7-4.6 |
| Number leaflets per leaf | | 3 | 3 | 3 |
| Leaf convexity | | Slight concave | Slight concave | Some flat, most slight concave |
| Shape leaflet base | | Rounded to obtuse | Obtuse | Obtuse |
| Leaf pubescence | | Medium density | Medium density | Light-moderate |
| Petiole pubescence | | Medium density | Medium density | Heavy density |
| Direction | | Perpendicular | Perpendicular | Perpendicular |
| Stipule length (mm) | Average | 35.74 | Not available | 23.3 |
| | Range | 30.2-39.7 | | 14-34 |
| Stipule anthocyanin coloration | | Yes | Weak yes | Yes |
| Leaf margins | | Serrate to crenate | Commonly crenate | Semi-pointed |
| Leaf color adaxial surface | | 364 U | 364 U | 5GY 5/6 |
| Leaf color abaxial surface | | 363 U | 370 U | 5GY 4/4 |
| Petiole color | | 366 U | 383 U | 5GY 7/10 |
| Leaf surface blistering | | Medium | Very weak | Medium |
| Leaf surface glossiness | | High | Medium | Low |

Flowering and Fruit

'Lucia' is a short-day variety that has ever-bearing tendencies under certain temperature and horticultural conditions. The primary flowers of 'Lucia' are smaller than those of 'Sweet Ann' but similar in size to those of 'Albion'. The flowers of 'Lucia' consistently exhibit five petals per bloom, as compared to 'Sweet Ann' and 'Albion' which exhibit greater variation, with flowers ranging from five to eight petals per bloom. In 'Lucia', the calyx is similar to 'Albion', but is smaller than in 'Sweet Ann'.

The exterior color of the fruit of 'Lucia' is slightly lighter than that of 'Sweet Ann' and lighter than 'Albion'. The fruit of 'Lucia' has excellent culinary qualities, including: uniform shape and size, lighter red color than 'Albion', and exceptional strawberry flavor. 'Lucia' produces very sweet fruit, having brix levels similar to 'Sweet Ann', but higher than 'Albion'.

In Table 3, comparative data for flower and fruit characteristics for 'Lucia', 'Sweet Ann' and 'Albion' are set forth.

TABLE 3

Flower and Fruit Characteristics of 'Lucia' Compared to 'Sweet Ann' and 'Albion'

| Characteristic | 'Lucia' | Cultivar 'Sweet Ann' | 'Albion' |
|---|---|---|---|
| Petal number | 5 | 5-6 | 5-8 |
| Petal length (mm): Average | 12.44 | 11.21 | 12.7 |
| Petal length (mm): Range | 10.6-14.3 | 9.2-13.13 | 11-15 |
| Petal width (mm): Average | 11.86 | 11.05 | 12.6 |
| Petal width (mm): Range | 10-13.1 | 9.0-13.10 | 11-14.0 |
| Position of flower (relative to foliage) | most exposed | most exposed, some even | most exposed, some even |
| Pedicel length (mm): Average | 430 | 330 | 113 |
| Pedicel length (mm): Range | 380-540 | 240-420 | 83-190 |
| Sepal color: Adaxial | 364 U | 364 U | 7.5GY 4/4 |
| Sepal color: Abaxial | 371 U | 370 U | 7.5GY 4/4 |
| Corolla diameter (mm): Average | 28.18 | 30.34 | 27 |
| Corolla diameter (mm): Range | 23.5-34.2 | 27.03-32.94 | 25-30 |
| Fruit color: External | 1788 C | 185 C | 5R 3/7 |
| Fruit color: Internal | 179 C | 1788 C | 7.5R 4/11 |

Leaf samples from 'Lucia', along with two advanced proprietary (unpatented) selections from the breeding program: '17J34' and '33K46', were submitted to a lab for allelic fingerprint comparison to the control variety, "Camarosa," and the over two hundred other varieties of strawberry in its data base. The allelic fingerprint analysis establishes that 'Lucia' is distinct and unique compared to the lab's large database of allelic fingerprints. Table 4 below sets forth the test results:

TABLE 4

Allelic Fingerprint Analysis

| Cultivar | M1 | M2 | M3 |
|---|---|---|---|
| 'Lucia' 42J4 | 202, 204, 206, 229 | 188, 216, 232 | 235, 241, 245, 269 |
| '17J34' | 204, 206, 214, 229 | 173, 190, 232 | 231, 243, 245, 265, 269 |
| '33K46' | 206, 224, 229 | 188, 190, 216, 232 | 235, 241, 245, 265 |
| 'Camarosa' | 214, 222, 224, 229 | 188, 190, 216, 232 | 247, 265 |

Performance

Performance with respect to fruit size, yield, and appearance for 'Lucia' was assessed by making comparisons with its male parent, 'Sweet Ann', and two advanced proprietary (unpatented) selections from the breeding program: '17J34' and '33K46'. All plants for these trials were initially grown at a high elevation nursery in Macdoel, Siskiyou County, Calif. The plants were dug on October 16$^{th}$, and planted after eleven days of supplemental storage on Oct. 27, 2012. The varieties were planted and evaluated at Elkhorn, Monterey County, Calif. The yield data for the comparisons are based upon 18,000 plants per acre, converted to yield in grams per plant. The fruit for these trials was harvested from April through August, 2013.

The average fruit size of 33.25 grams per berry for 'Lucia' is comparable to that of 'Albion' (33.0 g/berry), but smaller than that of 'Sweet Ann'. Fruit from 'Lucia' has great uniformity regarding size as compared to 'Sweet Ann'. The appearance of the 'Lucia' fruit is exceptional, even when overripe, as compared to other cultivars, maintaining its desirable characteristics during shipment of the fruit to market. The fruit from the trials was rated based upon commercial appearance using a scale wherein a numerical score of "5" represents the best appearance score. 'Lucia' rated superior, with a score of "4.5," to both 'Sweet Ann' and 'Albion', each of which have a commercial appearance rating of "4." Table 5 shows the performance of 'Lucia' compared to 'Sweet Ann', and the varieties designated '17J34' and '33K46'.

TABLE 5

Comparison of Performance of 'Lucia' to 'Sweet Ann' '17J34' and '33K46'

| Cultivar | Yield grams/plant | Size grams/berry | Appearance Rating 5 = Best |
|---|---|---|---|
| 'Lucia' | 1,057 | 33.25 | 4.5 |
| 'Sweet Ann' | 1,738 | 47.5 | 4.0 |
| '17J34' | 1,483 | 39.92 | 3.75 |
| '33K46' | 919 | 29.42 | 3.75 |

Disease and Pest Resistance

With the phase-out of methyl bromide as a soil fumigant, and the restrictions on use of less effective fumigants, strawberry varieties with high vigor and the ability to thrive and produce in non-fumigated ground have become increasingly more important. 'Lucia' has exhibited moderate tolerance to *Ramularia tulasnei* (common leaf spot) and *Sphaerotheca macularis* (powdery mildew). The new variety shows good tolerance to *Tetranychus urticae* (two spotted spider mite), and has continued to show good tolerance when grown in non-fumigated ground. 'Lucia' has also produced good results when grown in certified organic farms.

It is claimed:

1. I claim a new and distinct strawberry plant named 'Lucia' as herein described and illustrated by the characterizations set forth above.

* * * * *